United States Patent
Foroni et al.

(10) Patent No.: US 12,128,592 B2
(45) Date of Patent: Oct. 29, 2024

(54) MOULD AND A METHOD FOR FORMING AN ORTHOPAEDIC SPACER MADE OF MEDICAL CEMENT

(71) Applicant: G21 S.R.L., San Possidonio (IT)

(72) Inventors: Filippo Foroni, Mirandola (IT); Michele Ferrotto, Villar Perosa (IT); Riccardo Ferrotto, Frossasco (IT); Giuseppe Mulas, Modena (IT); Pietro Cavaliere, Messina (IT)

(73) Assignee: G21 S.R.L., San Possidonio (IT)

( * ) Notice: Subject to any disclaimer, the term of this patent is extended or adjusted under 35 U.S.C. 154(b) by 783 days.

(21) Appl. No.: 16/759,207

(22) PCT Filed: Jan. 22, 2018

(86) PCT No.: PCT/IB2018/050375
§ 371 (c)(1),
(2) Date: Apr. 24, 2020

(87) PCT Pub. No.: WO2018/203150
PCT Pub. Date: Nov. 8, 2018

(65) Prior Publication Data
US 2020/0316824 A1    Oct. 8, 2020

(30) Foreign Application Priority Data
May 4, 2017    (IT) .................... 102017000048295

(51) Int. Cl.
*B29C 39/10*    (2006.01)
*A61F 2/30*    (2006.01)
(Continued)

(52) U.S. Cl.
CPC ...... *B29C 45/0046* (2013.01); *A61F 2/30942* (2013.01); *A61F 2/30965* (2013.01);
(Continued)

(58) Field of Classification Search
CPC ......... B29L 2031/7532; B29K 2033/12; A61F 2310/00353; A61F 2002/30957;
(Continued)

(56) References Cited

U.S. PATENT DOCUMENTS 6,361,731 B1    3/2002    Smith et al.
7,789,646 B2    9/2010    Haney et al.
(Continued)

FOREIGN PATENT DOCUMENTS

EP    2522310       11/2012
EP    3245981 A1    11/2017
(Continued)

OTHER PUBLICATIONS

Communication of a Notice of Opposition dated Sep. 25, 2023 from European Patent Office Regarding Application No. EP18705020.8—Patent No. EP3618772, 63 pages.
(Continued)

*Primary Examiner* — Jamel M Nelson
(74) *Attorney, Agent, or Firm* — PEARNE & GORDON LLP

(57) ABSTRACT

The modular mould (1) for forming an orthopaedic spacer made of medical cement defines a moulding cavity delimited by a moulding surface (3, 3', 3") and configured for impressing a predetermined shape on said medical cement and realising said orthopaedic spacer. The mould (1, 1') comprises a first sector (7a, 7a', 7a"), defining a first portion of said surface, and a second sector (7b, 7b') defining a second portion of the surface, the first and the second portion of the surface being variable, so as to obtain spacers having variable dimensions.

8 Claims, 6 Drawing Sheets

(51) Int. Cl.
   *B29C 39/00* (2006.01)
   *B29C 39/26* (2006.01)
   *B29C 45/00* (2006.01)
   *A61F 2/36* (2006.01)
   *B29K 33/00* (2006.01)
   *B29L 31/00* (2006.01)

(52) U.S. Cl.
   CPC ............ *B29C 39/003* (2013.01); *B29C 39/26* (2013.01); *B29C 45/0001* (2013.01); *A61F 2002/30672* (2013.01); *A61F 2002/30957* (2013.01); *A61F 2/36* (2013.01); *A61F 2/3609* (2013.01); *A61F 2/3662* (2013.01); *A61F 2310/00353* (2013.01); *B29C 39/10* (2013.01); *B29K 2033/12* (2013.01); *B29L 2031/7532* (2013.01); *B32B 2274/00* (2013.01)

(58) Field of Classification Search
   CPC ............ A61F 2/30942; A61F 2/30965; B29C 39/003; B29C 39/26; B29C 39/10
   See application file for complete search history.

(56) References Cited

U.S. PATENT DOCUMENTS

| | | |
|---|---|---|
| 8,480,389 B2 | 7/2013 | Haney et al. |
| 8,801,983 B2 | 8/2014 | Haney et al. |
| 8,920,152 B2 | 12/2014 | Hawkins et al. |
| 9,937,047 B2 | 4/2018 | Holt et al. |
| 9,993,340 B2 | 6/2018 | Foroni et al. |
| 11,185,415 B2 | 11/2021 | Manotovi et al. |
| 2002/0025358 A1 | 2/2002 | Nelson et al. |
| 2007/0063378 A1 | 3/2007 | O'Donoghue |
| 2007/0222114 A1* | 9/2007 | Ziran ............... A61F 2/30942 |
| | | 264/279.1 |
| 2008/0015692 A1* | 1/2008 | Heinz ..................... A61F 2/44 |
| | | 623/17.11 |
| 2009/0146342 A1 | 6/2009 | Haney et al. |
| 2009/0157189 A1 | 6/2009 | Hartman et al. |
| 2010/0102484 A1 | 4/2010 | Haney et al. |
| 2010/0297276 A1 | 11/2010 | Haney et al. |
| 2012/0256344 A1 | 10/2012 | Stolarski et al. |
| 2013/0344186 A1 | 12/2013 | Haney et al. |
| 2016/0332328 A1* | 11/2016 | Wüst .................... A61F 2/3094 |
| 2018/0319057 A1 | 11/2018 | Foroni et al. |
| 2020/0316824 A1 | 10/2020 | Foroni et al. |

FOREIGN PATENT DOCUMENTS

| | | |
|---|---|---|
| EP | 3618772 B1 | 12/2022 |
| IT | 102017000048295 | 5/2017 |
| WO | 2009073781 | 6/2009 |
| WO | 2013086177 A1 | 6/2013 |
| WO | 2014072076 | 5/2014 |
| WO | 2016071939 A1 | 5/2016 |
| WO | 2017125832 A1 | 7/2017 |
| WO | 2018203150 A1 | 11/2018 |

OTHER PUBLICATIONS

Document in the name of Zimmer Biomet, "stageone-select-hip-cement-spacer-molds-surgical-technique", [cited Sep. 20, 2023] Availalbbe from [https://www.zimmerbiomet.com/content/dam/zimmer-biomet/medical-professionals/000-surgical-techniques/cements/stageone-select-hip-cement-spacer-molds-surgical-technique.pdf], 16 pages.

\* cited by examiner

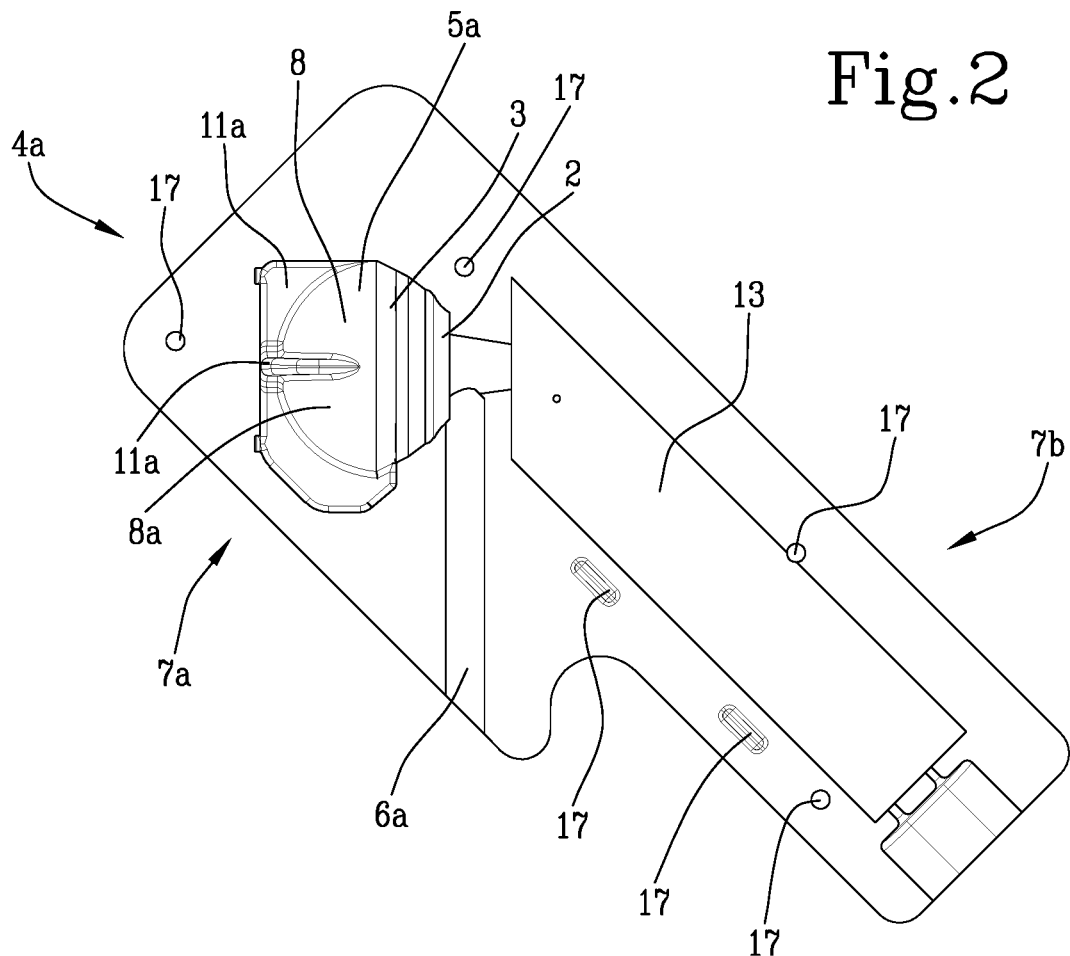
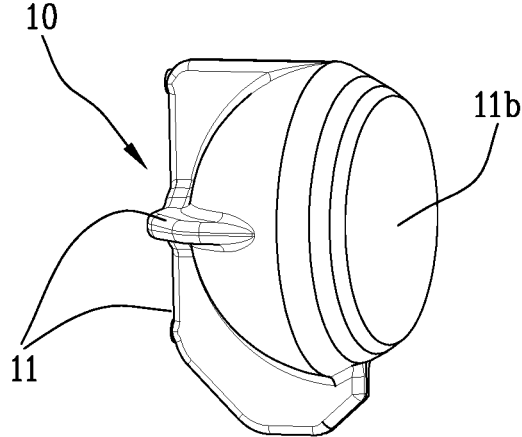

Fig.4
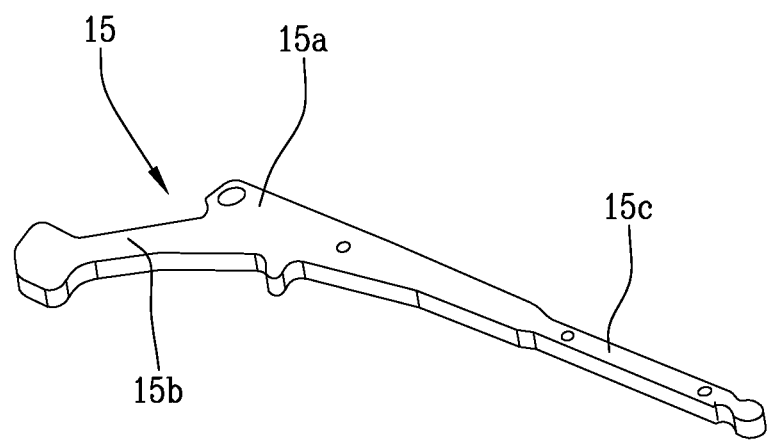
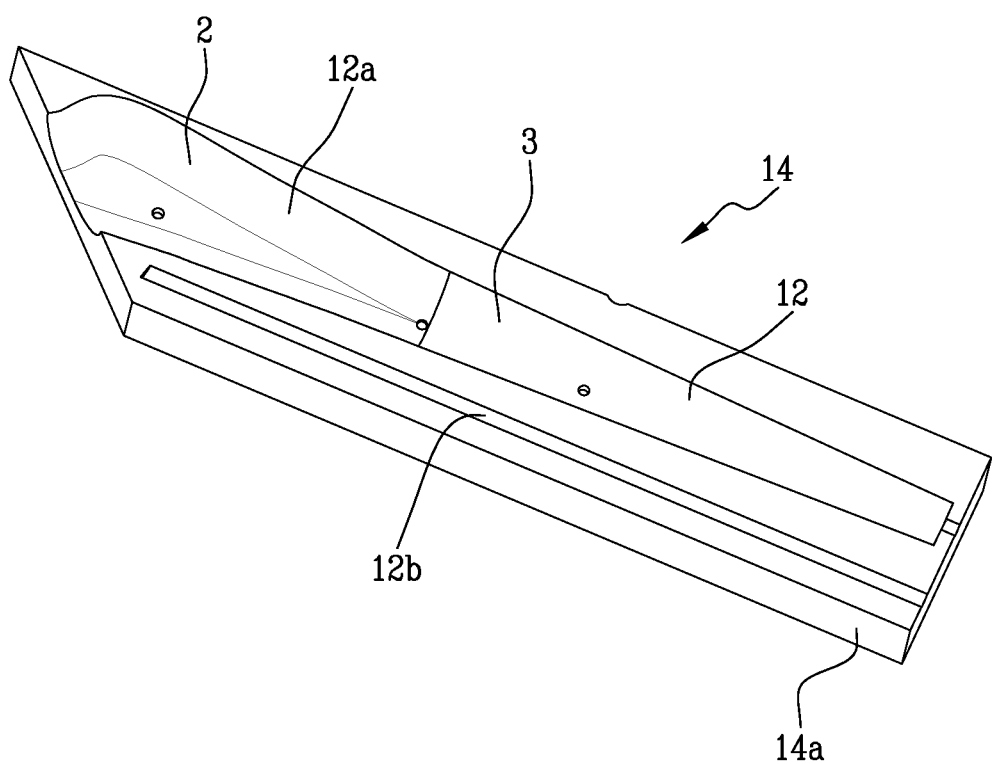

MOULD AND A METHOD FOR FORMING AN ORTHOPAEDIC SPACER MADE OF MEDICAL CEMENT

The present invention relates to a mould and a method for forming a temporary orthopaedic spacer.

As is known, orthopaedic spacers are made of medical bone cement and have the purpose of temporarily replacing fixed prostheses up to a conclusion of treatment for septic infections, or similar issues.

A prior art method for realising orthopaedic spacers includes modelling the starting bone cement directly in the operation theatre, so as to give the cement the predetermined shape.

In detail, with this method forming moulds are often used that comprise two moulding shells that are couplable to one another so as to realise a volume to be filled with the cement.

The shells can have shapes for realising a spacer that can be adapted to the shoulder, knee or hip joints, and others besides.

The known moulds disadvantageously enable only a partial flexibility of use.

In fact, the patients, as is well-known, have very different physiques and naturally require prostheses and spacers having dimensions corresponding to those of the limbs they will be used for.

Therefore, at present, either the surgeon uses a multiplicity of moulds for treating patients having different physiques or can treat only patients having those specific physiques which can be adapted to moulds placed on the market by manufacturers.

An aim of the present invention is therefore to make available a mould and a method for forming a temporary orthopaedic spacer which enable obviating the drawbacks of the prior art.

In particular an aim of the present invention is to provide a unitary modular mould which enables realising orthopaedic spacers different for patients having different physiques.

The stated technical task and specified aims are attained by a mould and a method for forming a temporary orthopaedic spacer according to the appended claims.

Further characteristics and advantages of the present invention will become more apparent from the indicative, and hence non-limiting, description of the mould and the method of the invention.

This description will be set out below with reference to the attached drawings, provided solely for indicative and therefore non-limiting purposes, in which:

FIG. 2 is a view from above of a first component of the mould of the previous figure;

FIG. 3 is a schematic representation of a second component of the mould of the previous figures;

FIG. 4 is a schematic representation of a third component of the mould of the previous figures;

Figure 1:
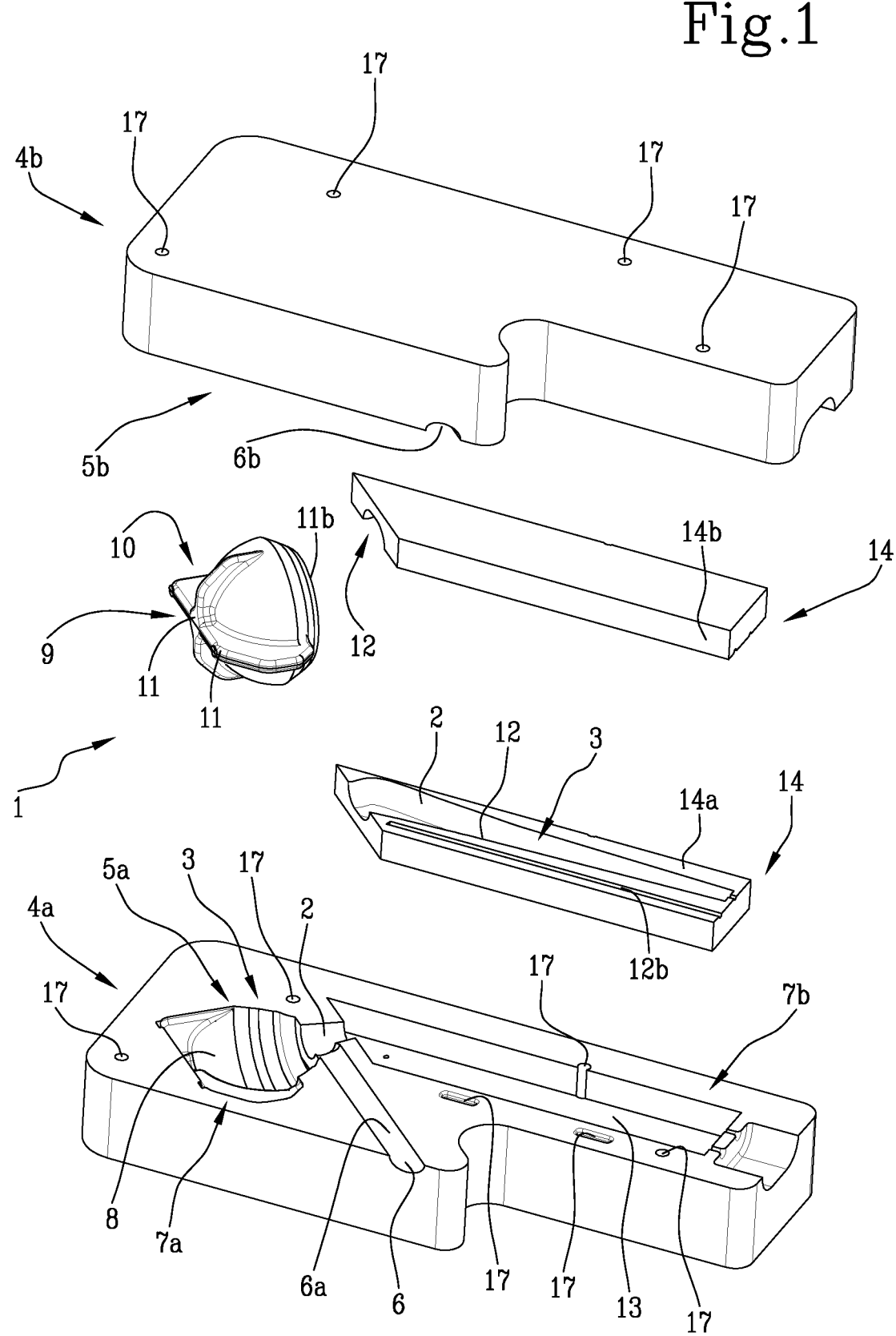
FIG. 1 is a schematic representation of the mould according to a first embodiment of the invention.

With reference to the accompanying figures, reference number 1 and 1' indicate a forming mould of an orthopaedic spacer made of medical cement, in accordance with the present invention.

The invention can also be used with known medical cements, which are however not described in detail in the following.

In general terms, the mould 1, 1' defines a moulding cavity 2 delimited by a moulding surface 3, 3', 3". The surface 3, 3', 3" is configured to impress a predetermined shape on the medical cement and to realise an orthopaedic spacer.

The mould 1, 1' proposed comprises at least a first sector 7a, 7a', 7a" defining at least a first portion 8, 3' of the moulding surface 3 and at least a second sector 7b, 7b', that defines at least a second portion 12, 3" of the surface 3, 3', 3".

The first and the second surface portion have variable configurations, so as to be able to obtain spacers of variable sizes and shapes.

To be precise, the first and the second surface portion are independently variable, according to methods explained below.

According to a first embodiment illustrated in FIGS. 1-4, the mould 1 comprises a first moulding element 4a and a second moulding element 4b. The first moulding element 4a comprises a first moulding surface 5a and the second element 4b comprises a second moulding surface 5b.

In particular, the first element 4a and the second element 4b are configured for being superposed on one another, at an open lateral surface which comprises the first surface 5a (in the case of the first element 4a) and the second surface 5b (in the case of the second element 4b).

In still greater detail, the two moulding elements 4a, 4b can be specular and therefore symmetrical with respect to a join plane, at which they contact to define the closed mould.

The first element 4a and the second element 4b together define a containing volume of the medical cement and further components able to form the spacer, which will be described in the following.

In the closed configuration of the mould 1, a passage hole 6 is defined that is shaped by a first channel 6a of the first element 4a and by a second channel 6b of the second element 4b (see for example FIG. 1).

The passage hole 6 enables inserting medical cement in liquid state into the mould 1.

The first moulding element 4a and/or the second moulding element 4b are preferably made of polypropylene or of a polypropylene based material.

Since, in the preferred embodiment of the invention, the first and the second element 4a, 4b are substantially specular, for simplicity of description, in the following a detailed description will be made of only the first element 4a, and what is described is also valid for the second element 4b, mutatis mutandis.

The first element 4a comprises a first sector 7a and a second sector 7b defining the moulding surface 3.

The first sector 7a, defines at least a first portion 8 of the moulding surface 3 and is for forming a first part of the orthopaedic spacer.

The mould preferably comprises a second forming insert 9 (illustrated in FIG. 3) suitable for inserting in the moulding cavity 2 of the mould 1.

In particular, the second forming insert 9 is insertable between the first portion 8 of the first moulding surface 5a of the first element 4a and the first portion 8 of the second moulding surface 5b of the second element 4b.

For the sake of precision, the second forming insert 9 has a complementary shape to a head portion 8a of the first portion 8.

In greater detail, the second forming insert 9 is configured for shaping the "head" of the spacer, i.e. the rounded part of the conformation destined to take the place of the missing epiphysis of the bone.

The second forming insert 9 preferably comprises positioning means 10 configured for enabling the correct insertion of the forming insert 9 in the first portion 8 of the first surface 5a (and/or the second surface 5b).

The positioning means 10 comprises at least a pair of ribs 11 in relief on an external surface of the second forming insert 9. In particular, the ribs 11 are suitable for being operatively inserted into respective profiled portions 11a of the first moulding element 4a and/or the second moulding element 4b.

In still greater detail, the second forming insert 9 has a forming surface shaped as a concave spherical cap shape 11b, so as to be able to impress, on the bone cement, the form of the head of the spacer.

Preferably, the second forming insert is made of a TPE-SEBS based material; this is however not a unique solution.

The second sector 7b defines a second portion 12 of the surface 3 and is for forming a second part of the orthopaedic spacer, adjacent to the first part.

In particular, the second sector 7b comprises a housing 13 in which at least a half-part 14a (illustrated in FIG. 4) is insertable, of at least a first forming insert 14 of the mould 1 (with reference to the second element 4b, reference will be made to the half-part 14b represented in FIG. 1 and complementary to the half-part 14a).

The half-part 14a comprises the second portion 12 of the surface 3 and has an elongate shape along a prevalent development direction configured for forming an elongate portion of the orthopaedic spacer in the superposed configuration of the first 4a and the second element 4b (and therefore in a superposed configuration of the half-part 14a and the half-part 14b, thus going to form the first forming insert 14).

The first forming insert 14 is preferably configured for forming a portion of rod or "stalk" of the orthopaedic spacer, i.e. the part having an elongate shape which is destined to couple with the residual diaphysis of the bone.

The second portion 12 of the surface 3 preferably has a tapered shape along the development direction in a distancing direction from the first portion 8.

Further, the second portion 12 of the surface 3 has a cone shape.

The mould 1 preferably comprises a plurality of first forming inserts 14 that are inter-replaceable, on the basis of the dimension of the spacer that is to be obtained.

In particular, each first forming insert 14 has a different width and/or length of the second portion 12, i.e. of the concave part, so as to realise orthopaedic spacers having different dimensions.

In practice, on the basis of the physical characteristics of the patient, spacers can be obtained having different transversal and/or longitudinal dimensions.

In the embodiment of FIG. 4, the second portion 12 of the surface 3 has the rod portion 12a and a conduit 12b configured for enabling insertion and distribution of the medical cement.

The first forming insert 14 is preferably made of a TPE-SEBS based material; this is however not a unique solution, as the first insert could also be made of polypropylene or another material besides.

As concerns the transversal dimensions of the spacer, the invention provides a good degree of modularity, as by replacing the first insert 14, spacers of different thickness can be obtained.

As concerns the longitudinal dimension, the invention enables a continuous modularity, as the length of the stalk or rod of the spacer is a direction function of the quantity of bone cement poured into the mould during the forming operations.

In fact, during the filling of the mould 1 with bone cement, the mould 1 is positioned so as to have the first portion 8 thereof inferiorly located with respect to the second portion 12, so that the passage hole 6 enables easy insertion of a portion of bone cement.

In this way it is possible to regulate, with absolute precision, the longitudinal dimensions of the second portion 12 on the basis of the volume of cement inserted through the hole 6.

The mould further comprises a reinforcing element 15 or "internal core", possibly of known type, insertable in the two forming inserts.

The reinforcing element 15 is preferably made of steel and is constituted by a profiled plate 15a, defined by a first portion 15b and a second portion 15c that are angled with respect to one another.

In this way, during the filling step of the mould 1 with the bone cement, the reinforcing element 15 is sunken into the cement, with the first portion 15b remaining sunken in the head of the spacer, while the second portion 15b is incorporated in the stalk.

The mould 1 comprises coupling means 17 configured for joining the first element 4a and the second element 4b in a superposed configuration of the first element 4a with the second element 4b. The coupling means 17 is conformed so as to join the first element 4a and the second element 4b by locking and/or jointing in order to position them correctly one on the other.

Once loaded with the medical cement (in the quantity necessary for obtaining the desired longitudinal dimensions), the mould 1 is pressed by a press of known type that is therefore not a part of the present description.

Once the cement has hardened, it defines the spacer with can therefore be removed from the mould and inserted in the patient's body.

The present invention relates to a method for forming an orthopaedic spacer.

The method, in a first version thereof, envisages providing a mould 1 realised in accordance with the first embodiment described above.

Therefore the first forming insert 14 and the second forming insert 9 are selected on the basis of the characteristics of the patient's physique, i.e. on the basis of the dimensions of the portions of bone on which the spacer intervenes.

A reinforcing element 15 is also predisposed, to be located internally of the two forming inserts, the dimensions of which element 15 are also a function of the physical characteristics of the patient.

At this point, the mould 1 is positioned so that the head portion 8a is located inferiorly of the rod portion 12a and the mould 1 is filled with bone cement, sliding the bone cement through the passage hole 6.

The quantity of cement inserted defines the longitudinal dimensions of the spacer.

The pressing step of the mould 1 then follows, and the consequent solidifying step of the bone cement, so as to obtain the desired spacer.

The mould 1 and the method described in the foregoing are able to obviate the drawbacks that have emerged in the prior art.

The above-mentioned mould 1 advantageously enables obtaining an orthopaedic spacer that is specific for a specific patient by modelling the head portion 8*a* by means of a second forming insert 9 and regulating the longitudinal and transversal dimensions of the rod portion 12*a* by means of the first forming insert 14.

Still more advantageously, the first forming insert 14 enables both obtaining a plurality of transversal dimensions that are different from the rod or "stalk" of the spacer, simply by replacing the first forming insert 14 with another forming insert 14, and obtaining any longitudinal dimension of the rod portion, in the above-explained ways.

Figure 5:
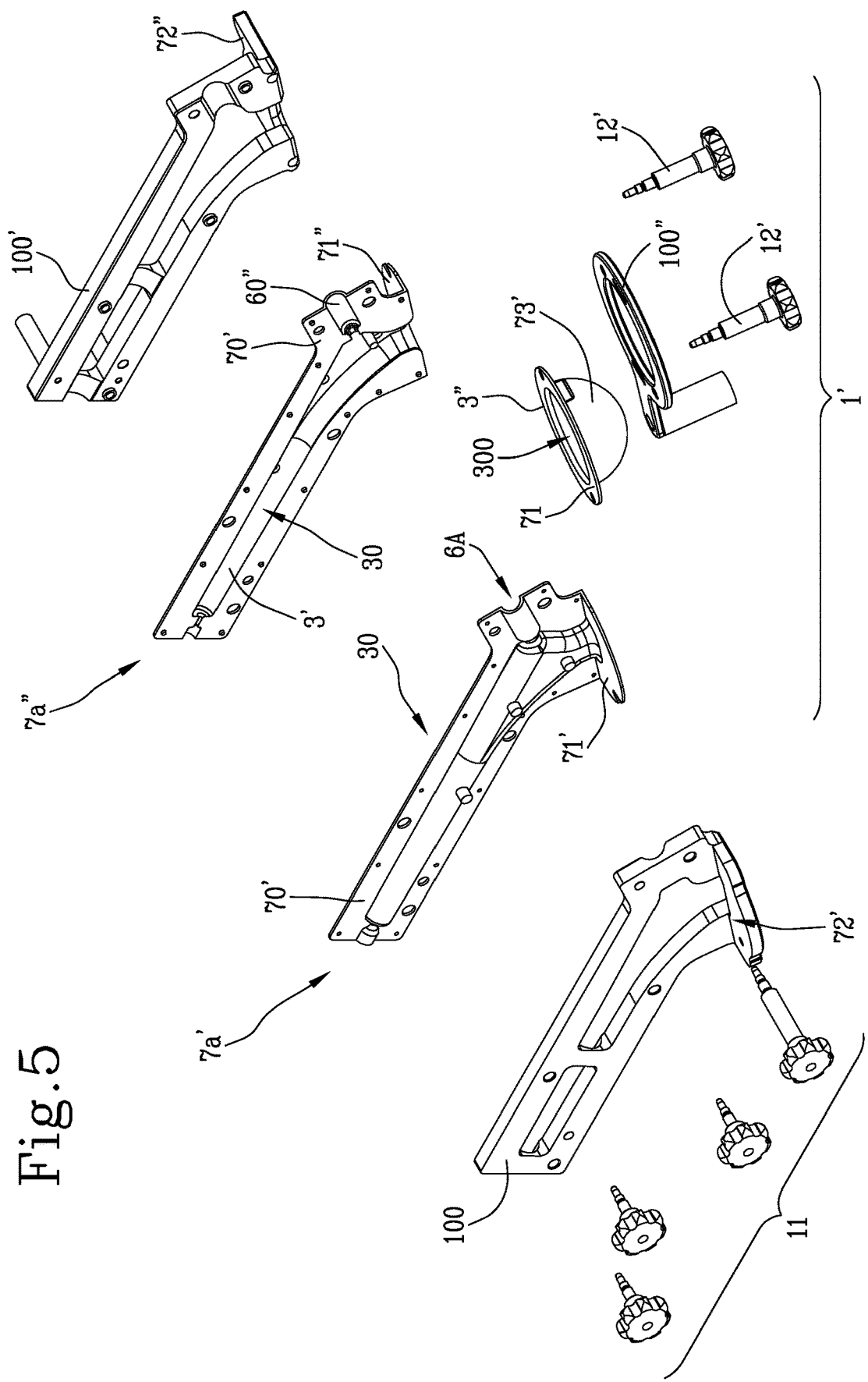
FIG. 5 is an exploded view of the mould according to a second embodiment of the invention, associated with a press.
Figure 6:
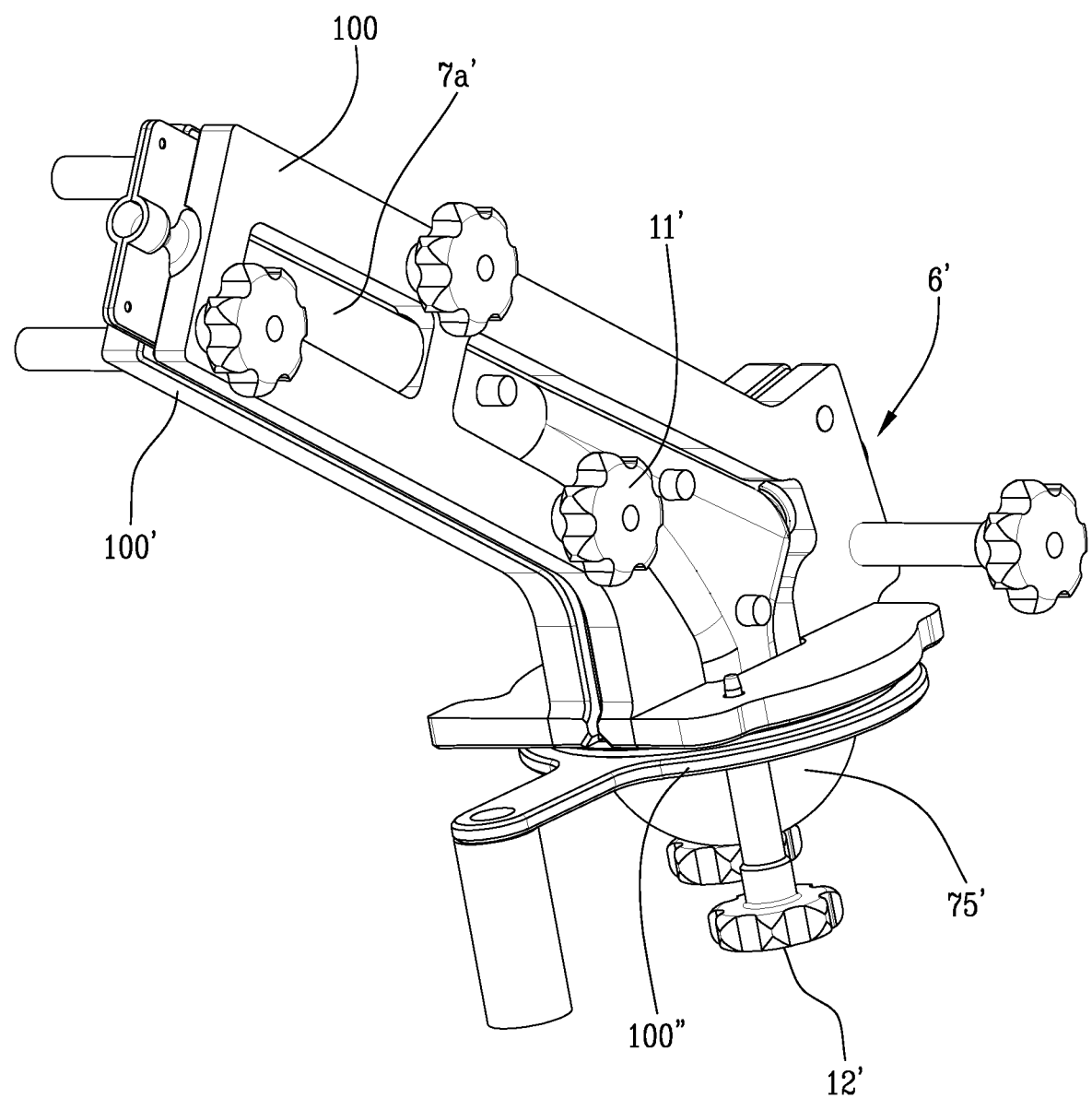
FIG. 6 is an overall view of the invention shown in the previous figure.

In accordance with a second embodiment of the invention, illustrated in FIGS. 5 and 6, the mould 1' includes a plurality of first sectors 7*a*', 7*a*" and second sectors 7*b*' replaceable and differently combinable.

The first sectors 7*a*', 7*a*" are intended for the forming of parts of stalk of the spacer and are equipped with respective surface portions 3' having different configurations, in particular dimensions, thus defining different stalk parts.

Also, in this case, as in the first embodiment, the first surface portion 3' is counter-shaped to the shape of the stalk, which assumes the conformation already explained previously.

Furthermore, the invention envisages a plurality of second sectors 7*b*', intended for the forming of head parts of the spacer and equipped with respective second surface portions 3", having different configurations, thus defining different head parts, especially with respect to the dimensions.

In practice, based on the stalk and head dimensions to be obtained, the user uses a different first sector 7*a*', 7*a*" and a different second sector 7*b*' on a case-by-case basis, so as to be able to realise a spacer that adapts, in terms of size and possibly shape, to the different needs of the specific patient.

Preferably, each first sector comprises a first and a second moulding element 7*a*', 7*a*", removably joinable, to define a partial forming cavity 30 for a spacer stalk, delimited by the first surface portion 3', 3".

As shown in FIGS. 5 and 6 the two moulding elements 7*a*', 7*a*" together form a blister structure and are adapted to be overlapped with each other, at a contact surface.

In still greater detail, the two moulding elements 7*a*', 7*a*" can be specular and therefore symmetrical with respect to a join plane, at which they contact to define a part of the closed mould 1'.

In the example represented, where the blister structure is shown, each moulding element 7*a*', 7*a*" conforms a peripheral flange 70', 70", which defines the mentioned contact surface and is adapted to the abutment with the flange 70', 70" of the other element.

Centrally to the flange 70', 70", the internal forming surface 3' is conformed, like a "footprint" of the stalk, i.e. comprising a concavity intended to face the concavity of the other moulding element 1'.

As can be seen in FIG. 5, such concavity may have a first substantially cylindrical part, possibly tapered towards an end, as already mentioned in relation to the first embodiment of the invention, which defines the stalk in the strict sense, while it has a fold in an elbow-like way towards the opposite end, so as to define the junction part between the stalk and head of the spacer.

The first element 4*a* and the second element 4*b* together define a containing volume of the medical cement and of the internal core 15 already mentioned above.

Each second sector includes a respective third moulding element 7*b*', comprising a forming concavity 300 that defines at least partially the second surface portion 3" and is intended for the forming of a spacer head.

Preferably, the third moulding element is a semi-spherical cap 7*b*', provided with an annular flange 71 at the mouth to the concavity 300.

In this case, at an end thereof, the first sector 7*a*', 7*a*" comprises a flange 71', 71" transversal to its longitudinal extension, which surrounds the internal forming cavity 30 of the stalk and is intended for contact with the annular flange 71 of the cap 7*b* in order to define a complete mould 1' for the spacer.

In even more detail, the first and the second moulding element 7*a*', 7*a*" of the forming blister of the stalk, each include their own half-flange 71', 71", so that, once joined, the complete flange of the first sector is obtained.

Therefore, the mould 1' has an open configuration (shown in FIG. 5), in which it is formed by three parts 7*a*', 7*a*", 7*b*', two specular moulding elements for the stalk, which together constitute the mentioned blister and then a third moulding element that is applied at one end of the blister.

In the closed configuration of the mould (shown in FIG. 6), a unitary internal cavity is obtained which is defined by the concave surfaces 3', 3" of the three moulding elements and is counter-shaped to the shape of the spacer to be obtained.

In the closed configuration of the mould 1, a passage hole 6' is defined that is formed by a first channel 6*a*' of the first element 7*a*' and by a second channel 6*a*" of the second element 7*a*".

The passage hole 6' enables inserting medical cement in liquid state into the mould 1'.

The advantage of the invention, also in this embodiment, is that the dimensions (and possibly also the shape) of the spacer are variable, since by choosing a different blister 7*a*', 7*a*" a different stalk can be obtained, for example with a different thickness; in the same way, by choosing a different cap 7*b*' a head with a different diameter is obtained.

By combining different blisters 7*a*', 7*a*" and different caps 7*b*' complete modularity can be obtained, which allows a multitude of spacers to be obtained realised according to the requirements of the specific patient.

It is to be noted that the invention may also envisage providing a plurality of internal cores 15 of different sizes, in particular lengths.

Figure 7:
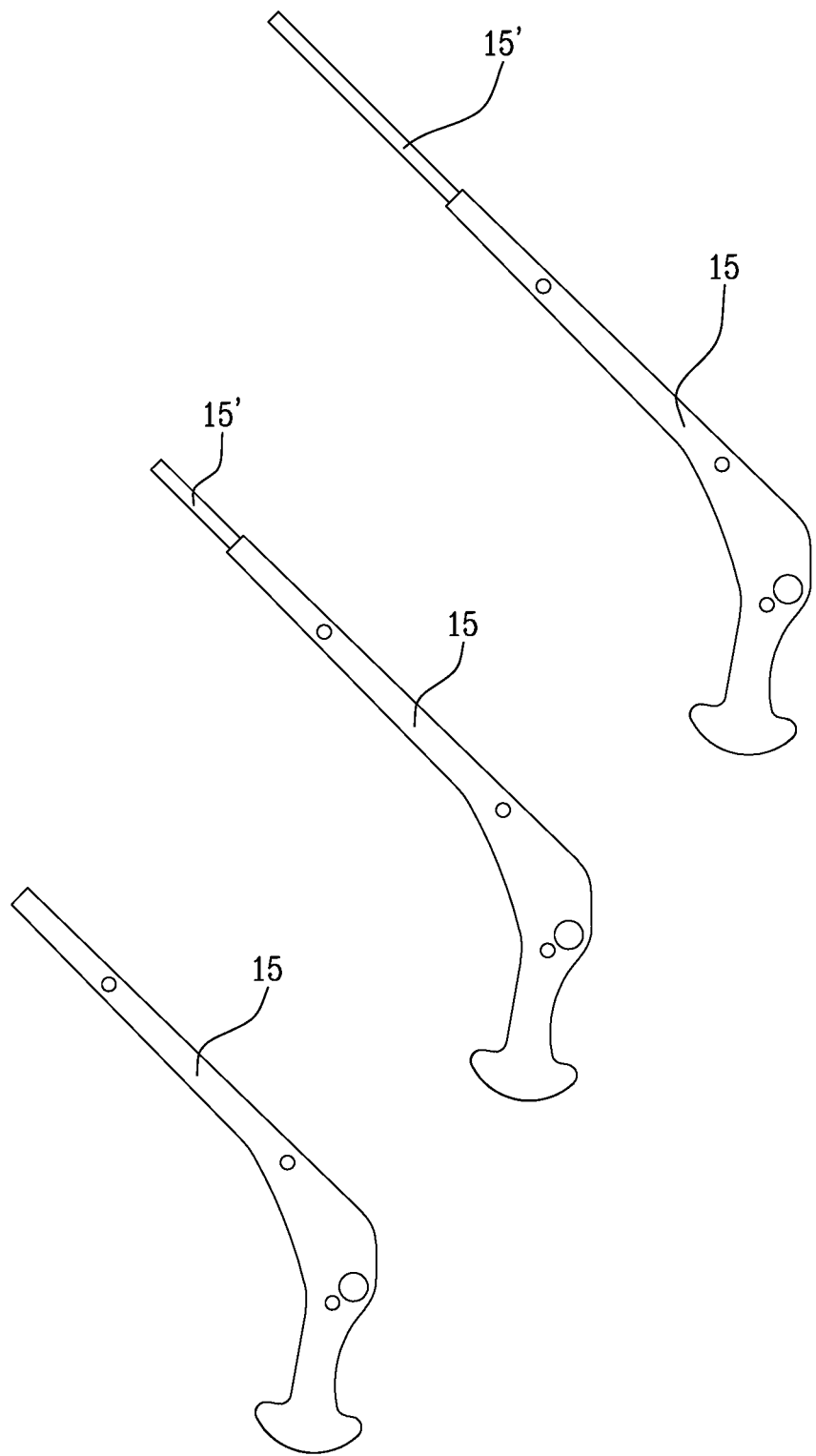
FIG. 7 shows a plurality of reinforcing elements, having different lengths, intended to be incorporated into the spacer realised by means of the invention.

In even more detail, as shown in FIG. 7, the length modularity of the reinforcing elements may be obtained through the application of extensions 15', comprising linear members of different lengths, that can be coupled to the core 15 so as to vary its total longitudinal dimensions.

Therefore, the invention also allows a modularity to be obtained of the reinforcing elements intended to be incorporated into the stalk of the spacer.

In this way, according to the specific patient, a core 15 can be chosen that is adapted to confer the right resistance to the stalk of the spacer; a greater length allows increased resistance along the longitudinal extension of the spacer.

The blister 7*a*', 7*a*" and the cap 7*b*' are preferably made of polypropylene or of a polypropylene based material.

For the purpose of realising the spacer, the invention envisages the use of a press that is used to give the mould 1' sufficient pressure for the correct forming of the spacer.

The proposed press includes three main components 100, 100', 100", preferably made of metal, intended to close and compress the mould 1'.

In detail, two lateral structures 100, 100' are provided, substantially specular, adapted to close the blister 7a', 7a" in a sandwich-like way on opposite sides, so as to compress it in an adjustable way.

For that purpose, adjusting screws generally indicated by 11' are provided, which allow the user to adjust the pressure that the two structures 100, 100' exert on opposite sides on the blister.

The lateral structures 100, 100', have a generally planar shape, with an outline alike to that of the first elements of the blister 7a', 7a", and may provide housing passages of the aforementioned footprints of the stalk, i.e. external convexities that, entirely, have the first surface portion 3' that is used to form the stalk of the spacer.

Furthermore, the press comprises a head structure 100", adapted to compress the head cap 7b', which may include a ring which internally receives the convexity of the cap 7b', which ring presses against the mentioned flange 71 of the cap 7b' which abuts with the flange 71', 71" of the blister 7a', 7a", which in turn abuts with a flange 72', 72" formed by the lateral structures 100, 100' of the press.

In detail, each lateral structure 100, 100' conforms its own half-flange 72', 72" in a way not dissimilar to the blister 7a', 7a".

The head structure 100" of the press is also equipped with adjusting screws, indicated by 12', which are used to adjust the pressure.

The process for realising the spacer through the use of the mould 1', realised in accordance with the second embodiment of the invention, envisages the following steps:

- choosing a first sector 7a', 7a" according to conformational and/or dimensional aspects of the stalk of the spacer to be formed;
- choosing a second sector 7b' according to conformational and/or dimensional aspects of the head of the spacer to be formed;
- choosing an internal core 15 according to the dimensions of the stalk to be formed;
- inserting the core 15 in the cavity 30 of the first sector 7a', 7a";
- joining the first and the second sector, so as to form the mould 1';
- inserting bone cement into the mould 1';
- pressing said mould 1', preferably with the press 100, 100', 100" of the invention; and
- once the bone cement has hardened, extracting the spacer formed from the mould 1'.

The invention claimed is:

1. A modular mould (1) for forming an orthopaedic spacer, the modular mould (1) comprising a first moulding element (4a) and a second moulding element (4b), wherein the first and second moulding elements (4a, 4b) together define a first moulding cavity (2), the first moulding cavity (2) having a first portion (8) and a second portion (12), the first portion (8) of the first moulding cavity (2) comprises one of a plurality of first forming inserts, the one first forming insert having a forming surface that defines a cavity which defines a first portion of the orthopaedic spacer, wherein the first portion of the orthopaedic spacer defined by the one first forming insert is different in size and/or shape than other first forming inserts of the plurality of first forming inserts; and wherein the second portion (12) of the first moulding cavity (2) comprises a pair of second forming inserts of a plurality of second forming inserts, the pair of second forming inserts positioned in a housing of the first and second moulding elements (4a, 4b), the pair of second forming inserts having a forming surface which together define a cavity which defines a second portion of the orthopaedic spacer, wherein the second portion of the orthopaedic spacer defined by the second pair of forming inserts is different in size and/or shape than other second forming inserts of the plurality of second forming inserts.

2. The modular mould (1) according to claim 1, further comprising, as part of a kit, said plurality of first forming inserts and said plurality of second forming inserts.

3. The modular mould (1) according to claim 2, wherein the parts of the kit are sized and configured to produce an orthopaedic spacer for a shoulder, knee or hip joint.

4. The modular mould (1) according to claim 2, wherein the first portion of the orthopaedic spacer is a head portion, and wherein the second portion of the orthopaedic spacer is a stalk portion.

5. The modular mould (1) according to claim 4, wherein the stalk portion has a tapered shape.

6. The modular mould (1) according to claim 2, further comprising, as part of the kit, one or more reinforcing elements (15), each of which is insertable within the first moulding cavity (2).

7. A method for forming an orthopaedic spacer comprising the following steps:
- providing the modular mould according to claim 1;
- choosing a first sector (7a', 7a") according to conformational and/or dimensional aspects of a stalk of the spacer to be formed;
- choosing a second sector (7b') according to conformational and/or dimensional aspects of a head of the spacer to be formed;
- choosing an internal core (15) according to the dimensions of the stalk to be formed;
- inserting a core (15) into a cavity (30) of the first sector (7a', 7a");
- joining the first and the second sector, so as to form the mould (1');
- inserting bone cement into the mould (1');
- pressing said mould (1'); and
- once the bone cement has hardened, extracting the spacer formed from the mould (1').

8. A method for forming an orthopaedic spacer comprising the steps of:
- providing the modular mould according to claim 1;
- predisposing a mould (1) for forming an orthopaedic spacer made of medical cement defining a moulding cavity (2) delimited by a moulding surface (3, 3', 3") configured for impressing a predetermined shape on said medical cement and for realising said orthopaedic spacer, said mould (1, 1') comprising at least a first sector (7a, 7a', 7a"), defining at least a first portion (8) of said surface (3), and a second sector (7b) defining at least a second portion of said surface, and at least a second sector (7b, 7b') defining at least a second portion of said surface, said first and second portion of the surface being variable, so as to obtain spacers of variable dimensions;
- providing said reinforcing element (15);
- choosing a first forming insert (14) from among a plurality of first forming inserts according to conformational and/or dimensional aspects of the desired spacer;
- providing a second forming insert (9);
- arranging said first forming insert (14) in said mould (1);
- arranging the second forming insert (9) in the mould;
- positioning the reinforcing element in the mould so that it is located in the first forming insert (14);
- inserting bone cement in said mould (1);
- pressing said mould (1); and once the bone cement has hardened, extracting the orthopaedic spacer from the mould.

* * * * *